United States Patent [19]

Seyl

[11] 4,123,335
[45] Oct. 31, 1978

[54] VOLTAGE MEASUREMENT WITH SPACED REFERENCE ELECTRODE

[76] Inventor: Rogert G. Seyl, 1123 Mulford St., Evanston, Ill. 60202

[21] Appl. No.: 825,282

[22] Filed: Aug. 17, 1977

Related U.S. Application Data

[63] Continuation-in-part of Ser. No. 654,854, Feb. 3, 1976, Pat. No. 4,060,461, and a continuation-in-part of Ser. No. 785,865, Apr. 7, 1977.

[51] Int. Cl.² ............... G01N 27/46; G01N 27/30
[52] U.S. Cl. ................................. 204/1 T; 204/195 C
[58] Field of Search ............ 204/1 C, 195 C; 324/29, 324/71 R

[56] References Cited

U.S. PATENT DOCUMENTS

| | | | |
|---|---|---|---|
| 3,748,247 | 7/1973 | Weisstuch | 204/195 C |
| 3,763,007 | 10/1973 | Seyl | 204/195 C |
| 3,893,026 | 7/1975 | Glazkov et al. | 324/72 |
| 4,003,815 | 1/1977 | Ikeda et al. | 204/195 C |

OTHER PUBLICATIONS

G. Lauer et al., "Effect of Uncompensated Resistance on Electrode Kinetic and Adsorption Studies by Chronocoulometry," Anal. Chem., vol. 38, pp. 1106–1112, (1966).

P. J. Moreland et al., "Technique & Instrumentation for Polarization Resistance Measurements," British Corrosion Journal, vol. 12, pp. 72–79, (1977).

D. A. Jones et al., "Polarization Methods for Measuring the Corrosion of Metals Buried Underground," J. Materials (USA) vol. 4, pp. 600, 602–605 (1969).

M. Prazak, "The Polarization Resistance Method for Corrosion Testing," Werkstoffe und Korrosion, vol. 25, pp. 104–112 (1974).

Primary Examiner—John H. Mack
Assistant Examiner—Aaron Weisstuch
Attorney, Agent, or Firm—McWilliams & Mann

[57] ABSTRACT

Method and device for accurately measuring polarization voltage of a measured electrode with a reference electrode in the form of an electrode in direct contact with the ionic conductor and separated in spacing from said measured electrode. The error of ionic conductor IR drop between measured and reference electrodes is corrected by a voltage of opposed polarity connected in series with said reference electrode, made proportional to the DC current polarizing said measured electrode, and adjusted in value to produce a characteristic 0.020 volt separation between transition points of line slope change in the measured initial range of the polarization current-potential relationship. Calibrating circuitry enables an X-Y recorder to accurately plot the current potential relationship.

24 Claims, 4 Drawing Figures

VOLTAGE MEASUREMENT WITH SPACED REFERENCE ELECTRODE

This application is a continuation-in-part of my pending patent application Ser. No. 654,854, filed Feb. 3, 1976, now U.S. Pat. No. 4,060,461 and is also a continuation-in-part of my pending patent application Ser. No. 785,865, filed Apr. 7, 1977.

BACKGROUND

This invention relates to methods and devices for measuring the corrosion of electronic conductors by non-gaseous ionic conductors, and is directed to correcting for ionic conductor resistance in said measurement.

More specifically, this invention is directed to method and means for correcting measurement error caused by ionic conductor resistance when corrosion current is measured by an electrode system including a measured electrode, a reference electrode, and an opposed electrode, as disclosed in my U.S. Pat. No. 3,694,324.

RELATED ART

The early art in electrochemistry recognized the need for excluding IR drop of ionic conduction in measuring electrode potential, and followed the practice of having ionic conduction from the reference electrode to the measured electrode pass through a glass capillary with its tip centered at the electrode area and separated from the measured electrode surface by a small distance such as the diameter of said capillary.

A number of practical considerations exclude the use of a reference electrode capillary in corrosion rate measurement. Its spacing to the electrode surface is too critical. Build-up of corrosion products interferes with such small spacing. The capillary is too fragile to withstand rate of liquid flow and impact of suspended matter which are frequently part of the corrosion system. The capillary tip measures only electrode surface in its immediate vicinity, while accelerated corrosion produces scattered localized areas of anodic and cathodic action which can operate at substantial potential differences.

In my U.S. Pat. No. 3,156,631, and as shown in FIG. 1 therein, the reference electrode was also disclosed in the form of a metal electrode in direct contact with the ionic conductor. It was separated from the surface of the measured electrode by a distance sufficient to include total polarization voltage produced on the measured electrode by the polarizing DC current, such as concentration, chemical, and mechanical polarizations. The separation distance from the surface of the measured electrode was stated to range from $\frac{1}{8}$ to $\frac{3}{4}$ inch. This spacing was discovered to produce a measured potential which averaged potential differences within the surface of the measured electrode. In-line positioning of reference, measured, and opposed electrodes, with the measured electrode in the center position, was also disclosed and shown as a means for minimizng error of IR drop through the ionic conductor.

In using the method of my U.S. Pat. No. 3,694,324 for measuring unaccelerated and accelerated corrosion rates, measurements of corrosion systems with relatively concentrated ionic conductors, such as waters from evaporative cooling water systems, showed substantially no error from ionic conductor resistance when measured from one measured electrode with a reference electrode.

With measurements made on relatively dilute corrosives such as surface water used for make-up in cooling water systems, corrosion currents measured from duplicated electrodes were significantly smaller than the currents measured from one measured electrode with a reference electrode.

A method and means was devised for correcting for ionic conductor IR drop between duplicated measured electrodes, as is most completely disclosed in my copending patent application Ser. No. 654,854, filed Feb. 3, 1976, now U.S. Pat. No. 4,060,461, and produced accurate measurement, while demonstrating that measurement with one measured electrode and reference electrode included a negative error arising from uncorrected ionic conductor IR drop.

With the method of this invention, both electrode systems accurately measure the corrosion rate of distilled water on steel electrodes.

SUMMARY OF INVENTION

Potential measurement with a reference electrode is made with circuitry drawing insignificantly small current, and the error voltage associated with ionic conduction $e_v$, is not caused by current passing to or from the reference electrode. Instead, the polarizing DC current $i_p$, passing between measured and opposed electrodes during corrosion current measurement establishes a field of potential gradient within the ionic conductor, and the value of $e_v$ is determined by the position of the reference electrode within this field. This can be expressed as, $e_v = k(i_p)(R_i)$, where $R_i$ is the ionic conductor resistance measured between the opposed and measured electrodes by an alternating current of frequency such as 400 Hz., and $k$ is determined by the location of the reference electrode within said field of potential gradient.

The error of ionic conduction is corrected for in the method and device of this invention by connecting in series with the reference electrode a circuit delivering a correction voltage $e_c$, of value maintained equal to $e_v$ and of polarity opposing $e_v$.

In one form of this invention, a current $i_p'$ is maintained through a correction circuit at the value $i_p' = i_p$ by continuous nulling against current $i_p$. Current $i_p'$ is passed through a resistance $R_i'$ in this circuit, with adjustment to $R_i' = R_i$ made at the time of starting the measurement. A fraction of the voltage drop across $R_i'$ is taken from a potentiometer setting $K_{ir}$ and delivered as the voltage $e_c$, so that $e_v = k(i_p)(R_i) = e_c = K_{ir}(i_p')(R_i')$. A variation of this form of the invention utilizes the resistance correcting circuit of said pending patent application Ser. No. 654,854.

In another form of this invention, simplified through the elimination of said nulled correction circuit, a potentiometer is connected across opposed electrode O and measured electrode M, and the correction voltage $e_c$, is taken as a fraction $K_{ir}'$, of the voltage across this potentiometer from its connection at M.

It would be possible to determine the approximate value of $K_{ir}$ or $K_{ir}'$ from a preceding corrosion current measurement made with duplicated measured electrodes when operated with full ionic conductor resistance correction. Instead, it is preferred that the device of this invention can be operated independently of other corrosion current measurements through the criteria of adjusting $K_{ir}$ or $K_{ir}'$ to the value producing the characteristic 0.020 volt separation between consecutive transition points of line slope change in the measured initial range of current-potential relationship. When accelerated corrosion occurs, the center of the line of steepest $e/i$ slope then measures the cathodic protection potential that eliminates the acceleration, and its slope measures and indicates the corrosion rate then remaining.

OBJECTS

One object of this invention includes method and means for continuous and accurate correction of the error of ionic conductor IR drop occurring with electrode potential measurement made from a reference electrode in the form of a metal electrode directly immersed in the ionic conductor and spaced from a measured electrode which undergoes polarization through a range of applied polarization current measurement.

Another object is the inclusion in said continuous correction, of the IR drop of electronic conduction through the lead wire conducting the polarizing current from the measurement device to the electrode undergoing the polarization.

A further object is a simplified form of device for the continous correction of the errors of said IR drops.

An additional object is the inclusion in said corrosion current measurement circuit of means for calibrating an X-Y recorder which measures the range of current-potential relationship, from the microammeter in said corrosion current measurement.

THE FIGURES

DISCLOSURE

Significance of $R_i$

A relationship between a full range of corrosion current encountered in measurement practice and an ohmic value of an ionic conductor would indicate the extent to which ionic conductor resistance operates as a factor tending to introduce error in corrosion current measurement. For this purpose, it is not easy to view the corrosion performance of the electronic-ionic conductor interface in full perspective, due to its scope and complexity. Performance of the system is determined by many factors including metal composition and heat treatment, ionic conductor composition such as pH, factors of environment including temperature and flow rate of the ionic conductor, the possible presence of corrosion inhibitors or corrosion accelerators, and the combined effect of these factors operating through the passage of time.

As a consequence, this relationship is expressed in Table 1 below, in the form of generalization of reasonable probability, based upon present experimental background. Rate-determining corrosion current $i_R$, refers for example, to a cylindrical electrode of 4.0 mm. diameter, 32 mm. exposed length, and 4.0 sq. cm. exposed area. Ohmic resistance $R_i$, is measurable between two such electrodes positioned with major axes parallel and at 9 mm. separation distance, by an AC current at a frequency such as 400 Hz.

The voltage drop, $(i_R)$ $(R_i)$, indicates that, in general, the need for correction for ionic conductor resistance may be expected for every corrosion system measured.

TABLE 1

| Range Nr. | $i_R$ vs. $R_i$, Generalized | | |
|---|---|---|---|
| | $i_R$, mmA | $R_i$, Ohms | $i_R (R_i)$, Volts |
| 1 | 1 | 50,000 | 0.05 |
| 2 | 10 | 5,000 | 0.05 |
| 3 | 100 | 500 | 0.05 |
| 4 | 1,000 | 50 | 0.05 |

In practice, some marked exceptions to Table 1 are encountered in both directions of deviation. A concentrated sodium chloride solution with iron electrodes produces an IR drop of only (20 mmA) (50 ohm) = 0.001 volt, while one drop of sulphuric acid per liter of distilled water produces an IR drop of (200 mmA) (500 ohm) = 0.10 volt. However, such exceptions are not generally sufficient to negate the usefulness of the above generalization.

FIG. 1

Figure 3:
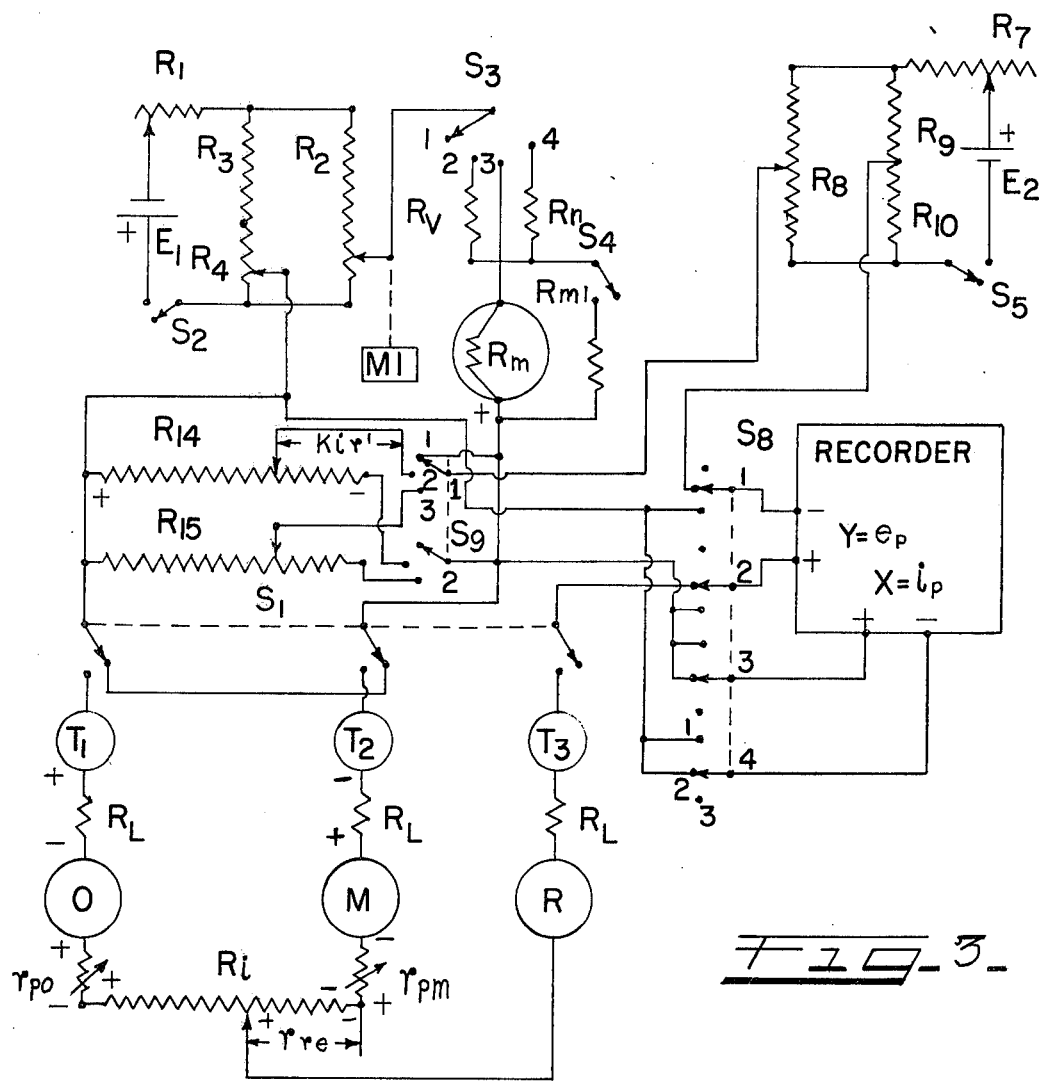
FIG. 3 is the circuit diagram of a simplified alternative means for correcting for said IR drop.

Measurement by the method of this invention is made in the form of an X-Y recording, as shown in FIG. 3 of said U.S. Pat. No. 3,694,324 (hereinafter the 3,694,324 patent). The purpose of FIG. 1 herein is to show the effect of measurement, made without correction for ionic conductor IR drop in the potential measurement, and later, to explain in part the operation of the method and device of this invention.

Figure 1:
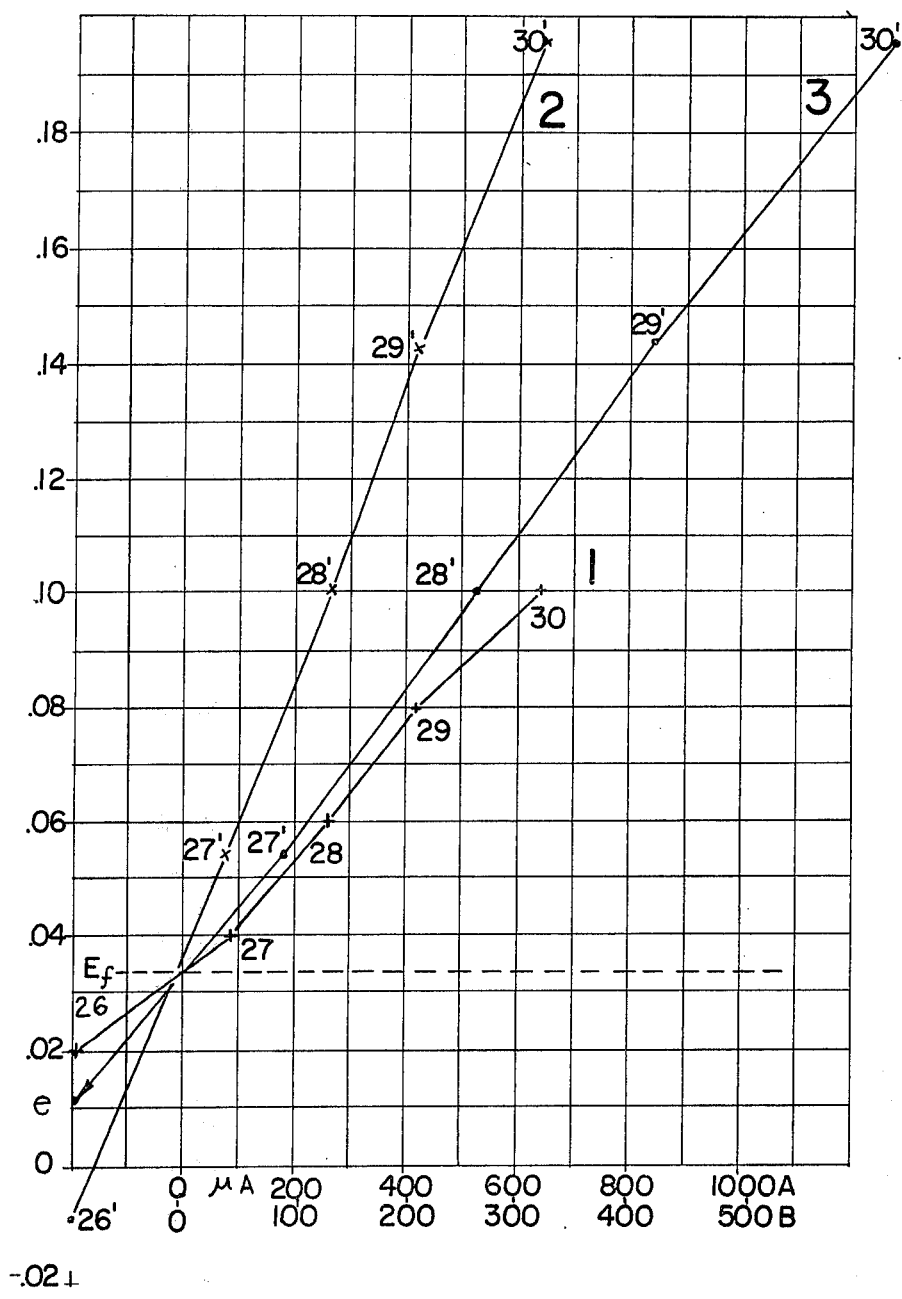
FIG. 1 illustrates current-potential relationship measured with and without correction for ionic conductor IR drop in the measurement of potential.

In FIG. 1 herein, current-potential relationship 1 illustrates measurement made of an accelerated rate in the absence of ionic conductor IR drop in the potential measurement. The transition points 26 through 30 are taken at the measureable values of polarizing current $i_p$ and polarized electrode potential $e_m$ shown in FIG. 1 of the 3,694,324 patent. The current units shown in said patent are herein regarded as microamperes, and the values of $i_p$ and $e_m$ are tabulated in Table 2 below. Relationship 1 is plotted from current scale A.

TABLE 2

| Data Plotted in Figure 1 | | | | |
|---|---|---|---|---|
| Transition Point | $e_m$ Volts | $i_p$ mmA | $e_v = i_p(150)$ Volts | $e'_m = e_m + e_v$ Volts |
| 26 | .020 | −190 | .0285 | −.0085 |
| 27 | .040 | 90 | .0135 | .0535 |
| 28 | .060 | 265 | .0398 | .0998 |
| 29 | .080 | 420 | .0630 | .1430 |
| 30 | .100 | 645 | .0968 | .1968 |

The following corrosion current measurements are made from said relationship 1, according to method disclosed in the 3,694,324 patent. Corrosion current $i_A$, measured at the free electrode potential $E_f$ at which the undisturbed corrosion occurs, is measured as, $i_A = \frac{1}{2}(i_a + i_c)$ $(\frac{1}{2}E_d/e_p)$. At $e_p = 0.01$ volt of anodic polarization, $i_a = 140$ mmA, and at 0.010 volt of cathodic polarization, $i_c = 120$ mmA, from which $i_A = \frac{1}{2}(140 + 120)$ $(0.015/0.010) = 195$ mmA. Corrosion current $i_B$ is measured from the line of steepest slope, found here between transition points 28 and 29. At $\frac{1}{2}E_d = 0.015$ volt, $i_B$ is measured as 117 mmA. The rate-determining corrosion current $i_R$, is then calculated as, $i_R = 2.4(i_A) - i_B = 2.4(195) - 117 = 351$ mmA. Current $i_{xb} = i_R$, measured at the center of the line of steepest slope, is 343 mmA, and shows close agreement.

Relationship 2 of FIG. 1 illustrates measurement made when ionic conductor error voltage $e_v = ki_p)$ ($R_i$), is included in potential measured by the reference electrode. In view of Table 1 above, and by way of illustration, the value $R_i = 500$ ohms, is assumed to be measurable between the measured and opposed electrodes. Consequent values for $e_v$ are arrived at as follows.

The value of $k$ is in theory determined from parameters of electrode probe design, but the possibility of accurately calculating its value encounters problems such as undeveloped mathematical treatment, the probability of laborious calculations, and the need for verification through experimental correlation with weighed metal loss. Much more expedient is use of the circuitry that operates through the relationship $e_v = k(i_p) (R_i) = K_{ir}(i_p') (R_i')$, with circuit values selected for $i_p' = i_p$ and $R_i' = R_i$, so that $k = K_{ir}$. With each measurement made during progress of the corrosion, $K_{ir}$ is adjusted according to the criteria that its value produces the characteristic 0.020 volt separation between transition points of line slope change. By this method, and with the probe design described below, it is found that value of $K_{ir}$ is generally about 0.3, but varies somewhat with corrosion interface composition and with progress of the corrosion. For the purpose of FIG. 1, the value is taken of $k = 0.3$, so that $e_v = 0.3(i_p) (500)$. Table 2 includes the values of $e_v = i_p(150)$, and the values of $e_m' = e_m + e_v$ that would be measured. Relationship 2 of FIG. 1 is a plot of $e_m'$ against $i_p$ referred to current scale A.

However, in measuring the X-Y relationship by recording according to said patent, size of current unit is selected to produce an approximately 45° slope of the relationship as it passes through free electrode potential $E_f$, to obtain graphical precision in both $e_p$ and $i_p$ measurement. In FIG. 1, current axis B is selected to meet this requirement, and the X-Y recording of relationship 3 is plotted therefrom.

Corrosion current measurements obtained from relationship 3 might be viewed with both confusion and alarm. Transition points 27' and 29' occur at sufficient difference of line slope to be clearly recognized, but if viewed from X-Y recording made within precisions of ±0.001 volt, and ±1.0 mmA on the B current scale, transition point 28' might not be recognized. Instead of finding transition points occurring at the 0.020 volt separations, the observation would be made of a 0.1430 −0.0535 = 0.0895 volt separation. Measurement of $i_A = 70$ mmA at potential $E_f$ and of $i_B = 55$ mmA from the slope of the line between points 27' and 29', indicates that $i_R = 2.4(70) -55 = 113$ mmA. Measurement from the center point of the line between points 27 and 29 indicates $i_{xb} = 295$ mmA. The large disagreement between the two indicated values for $i_R$ should cause alarm, and the entire recording might be regarded as evidencing lack of measurement method precision, a view that would be further evidenced in attempting correlation with weighed metal loss.

The consequence of eliminating error voltage $e_v$, through the method and device of this invention, is to reduce the potentials of transition points 26', 27', 28' and 29' to the potentials of points 26, 27, 28 and 29. Although in relationship 3, this causes line slope through potential $E_f$ to be only about 18°, transition point 28 becomes measurable. If greater graphical precision is required, measurement can be repeated with current scale A, to produce relationship 1 of FIG. 1.

Electrode Probe

Viewed broadly, the effect of increase in resistance of ionic conductor is to impose more critical requirements on probe design, and spacing of electrode surface from containing wall of ionic conductor, including liquid surface, to thereby minimize disturbance of the field of current conduction that is required for uniformity of polarized electrode potential. A preferred form of electrode probe is disclosed in my pending patent application Ser. No. 785,865, filed Apr. 7, 1977. Removable cylindrical electrodes are positioned within the ionic conductor by insulators of the same diameter as the electrodes, to minimize interference with lines of ionic conductor flow past the electrodes and with the field of current conduction between the electrodes. Top and bottom ends of the electrodes are shielded by a means substantially eliminating crevice corrosion at the shielding boundary. Alternative forms of construction permit operation in the presence of ionic conduction flow, and at elevated pressure.

One form of electrode probe used in the method of this invention includes a measured, an opposed, and a reference electrode, all made from the metal selected to undergo the corrosion, so that corrosion products introduce no foreign substances. The measured and opposed electrodes are of 4 mm diameter, and the reference electrode is of 2 mm diameter to reduce ionic conductor IR drop across its diameter. The three electrodes are positioned with major axes parallel and in the same plane, at a separation distance of 9 mm, and with the measured electrode in the middle position. The electrodes are shielded at top and bottom to expose an electrode surface of 32 mm length, and are immersed in the ionic conductor with top electrode surface at least 30 mm below liquid level and with glass container wall at least 30 mm from electrode surface, to assure full paths of conduction within the ionic conductor.

When the corrosion system includes flow of ionic conductor with dissolved oxygen, it is frequently observed that upstream electrode surface becomes cathodic and downstream electrode surface becomes anodic and may develop adherent corrosion products. In addition, with substantially neutral waters containing dissolved calcium and magnesium, a carbonate scale can form on the cathodic area. These differences between upstream and downstream surfaces call for positioning the plane in which the electrodes are mounted in the position perpendicular to the direction of flow, to expose each electrode to undisturbed lines of flow and to substantially the same rate of flow, and so that the reference electrode can measure the averaged potential of the anodic and cathodic areas.

The method and device of this invention are not restricted to a probe of the above form and mode of operation. The method permis correction for error voltage $e_v$, when the reference electrode is located other than in the same plane as the measured and opposed electrodes. The development of areas of localized anodic and cathodic action with respect to direction of ionic conductor flow can be eliminated if desired, by slow rotation of the electrode probe. The probe can include a fourth electrode, operated as an anode when the measured and opposed electrodes are to be operated as duplicated measured electrodes through additional measurements.

FIGURE 2

Figure 2:
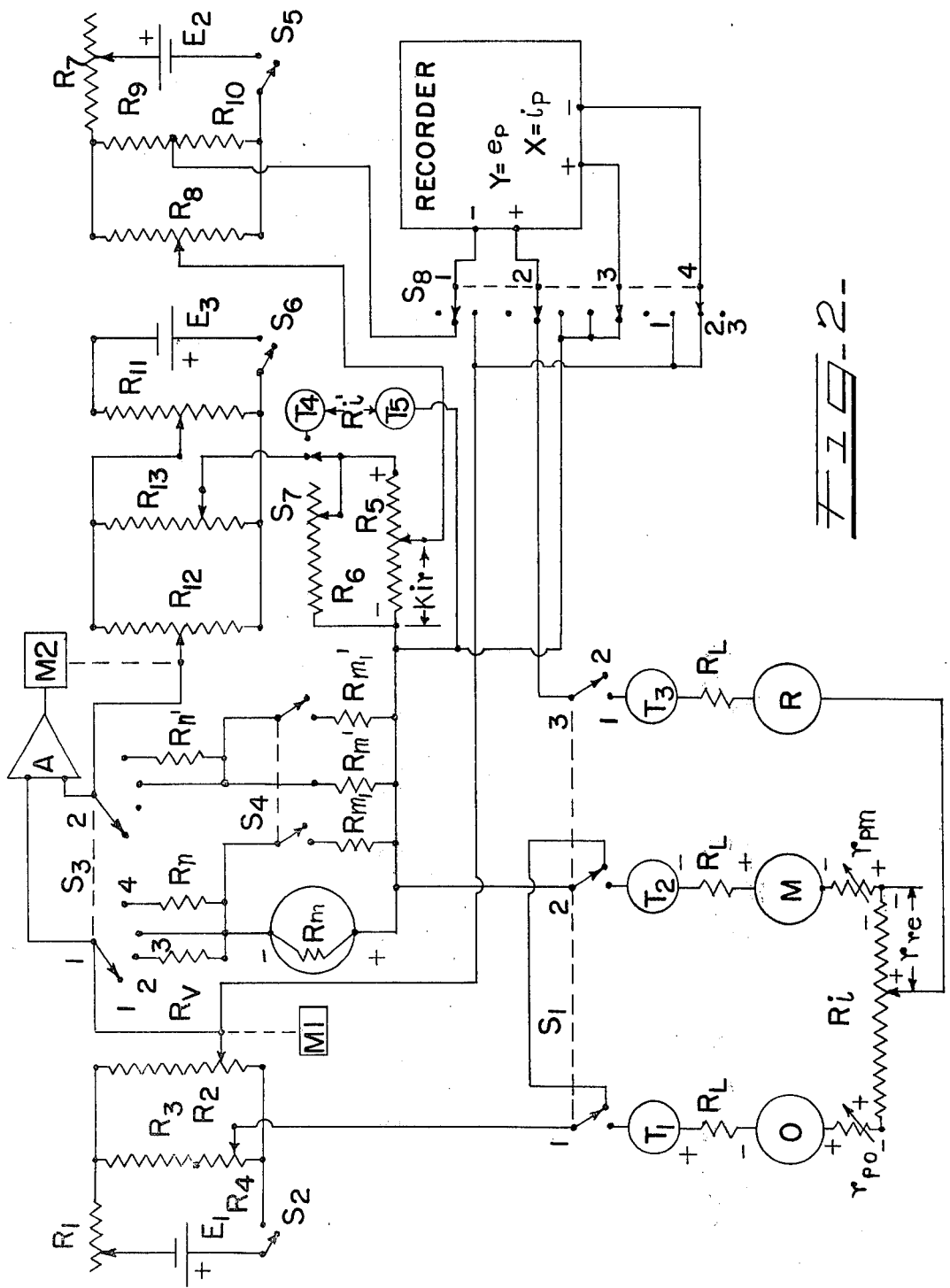
FIG. 2 is the circuit diagram of an accurate means for correcting for said IR drop.

Illustrated in FIG. 2 is the preferred embodiment of my present invention in the form of a circuit diagram of a device that corrects for error voltage $e_v$ through voltage nulling circuitry that maintains current $i_p' = i_p$, through resistor $R_i' = R_i$, with correction voltage $e_c$ taken as $e_c = K_{ir}(i_p')(R_i')$. Its features include means for providing ample sensitivity for measuring the smallest corrosion currents, circuitry that tends to maintain the value of $K_{ir}$ unchanged during changes in value of $R_i$ and cathodic polarization resistance $r_{pm}$ that usually develop during progress of the corrosion, and calibration of the X-Y recorder from the microampere meter measuring $i_p$, in units of voltage and current selected to accurately fit graph paper rulings of varied selected sizes.

The measured corrosion system includes measured electrode M of polarization resistance $r_{pm}$, opposed electrode O of polarization resistance $r_{po}$, and reference electrode R, which operates through null measurement and so remains substantially unpolarized. Polarization resistances $r_{pm}$ and $r_{po}$ are shown as variable consequent to their operation expressed through the Interface Electrode System. Ionic conductor resistance between electrodes O and M is shown as $R_i$. It is measured by an AC voltage at about 400 Hz or more, which excludes $r_{pm}$ and $r_{po}$ from the measurement, but includes lead wire resistance $R_L$ connecting the electrodes to respective device terminals. Ionic conductor resistance between measured electrode M and reference electrode R is shown diagramatically as $r_{re}$, defined as $e_v = i_p(r_{re})$, and is determined primarily by electrode probe design.

In FIG. 2, the circuitry for DC voltage delivery and for polarizing current measurement comprises the following. Switch $S_1$ in position 1, connects the electrodes to the device. Switch $S_2$ connects battery $E_1$ through dropping resistor $R_1$, to across potentiometer $R_2$ and to across the series connection of resistor $R_3$ with potentiometer $R_4$. The arm of potentiometer $R_4$ connects to opposed electrode O. Motor $M_1$ is geared through a clutch release mechanism, to drive the arm of potentiometer $R_2$ at a constant speed and at a selected rate of full arm travel such as 30 minutes. A dial attached to said arm is calibrated with a scale such as $-5$, through 0, to +25 minutes. The arm of potentiometer $R_2$ is connected through switch $S_3$ in position 3, and through a microammeter of DC resistance $R_m$, to measured electrode M. Switch $S_4$ connects current multiplier resistance $R_{ml}$ across the microammeter, and illustrates the use of a plurality of such resistors required to cover the entire range of measurable corrosion current. The voltage to the current recording axis X, is taken between the arm of potentiometer $R_2$ and the positive pole of the microammeter. Switch $S_3$, in position 4, connects a current sensitivity resistor $R_n$ in series with the microammeter to increase the voltage from which small currents are measured, and illustrates a plurality of such resistors that can be used as required.

In FIG. 2, the potential measuring circuit, exclusive of the error correcting circuitry, comprises the following. One voltage lead to the voltage recording Y axis is from reference electrode R, through switch $S_1$. In the presence of accelerated corrosion, potential difference between electrodes M and R during initial hours of corrosion may be substantial, and far beyond the movable zero position control of the recorder. Such voltage difference is opposed by the voltage equalizing circuit of switch $S_5$ connecting battery $E_2$, through dropping resistor $R_7$, across potentiometer $R_8$ and across the series connection of resistors $R_9$ and $R_{10}$ of equal value. The other voltage lead to the voltage recording Y axis is from measured electrode M, through lead wire resistance $R_L$, through switch $S_1$, and through said voltage equalizing circuit. The error correcting circuitry is removed from measurement when desired, by positioning the arm of $R_5$ to the end connected to the microammeter.

In FIG. 2, circuitry for introducing correction voltage $e_c$, includes the following. The closing of switch $S_6$ connects battery $E_3$ across potentiometer $R_{11}$. The arm of $R_{11}$ delivers selectable voltage across potentiometers $R_{12}$ and $R_{13}$. The voltage between the arms of potentiometers $R_{12}$ and $R_{13}$ is applied across the series circuit comprising pole 2 of switch $S_3$, resistor $R_m'$, and the variable parallel connection of potentiometer $R_5$ to potentiometer $R_6$. Voltage difference between the arms of switch $S_3$ is fed to amplifier A driving motor $M_2$ which is geared to the arm of potentiometer $R_{12}$, to maintain zero voltage difference between the arms of said switch $S_3$. Resistors developing nulling voltage drops are selected to duplicate those in the microammeter circuit, and include $R_m' = R_m$, $R_{ml}' = R_{ml}$, and $R_n' = R_n$, so that a current $i_p'$ in the nulling circuit equals polarizing current $i_p$ through the microammeter, in both value and polarity. The maximum parallel resistance of potentiometers $R_5$ and $R_6$, which are of equal resistance, is selected to equal the maximum value of $R_i$ encountered in general practice, and shown in Table 1 as 50,000 ohms. A dial on the arm of potentiometer $R_5$ is calibrated in units from 0.00 to 1.00, with zero at the end connected to the plus terminal of the microammeter. $K_{ir}$ is measured as the setting and reading of this dial. Amplifier A includes a gain control to match the range of sensitivity requirements. It also includes an input disconnect switch, and means for then balancing its output for zero motion of motor $M_2$. The arm of potentiometer $R_{12}$ includes a position indicating display from which motion of motor $M_2$ is indicated. This display also includes a zero position point to which adjustment of the arm of potentiometer $R_{13}$ is made, to divide anodic nulling from cathodic. The precision of Y axis voltage nulling is additionally determined by the precision of this $e_c$ voltage delivery nulling circuit. For each change made in X axis current range, the position of the arm of potentiometer $R_{11}$ should be correspondingly changed to assure travel of the arm of potentiometer $R_{12}$ sufficient for precision nulling, as shown from said position indicating display.

Each axis of the X-Y recorder is of the potentiometric null type that draws substantially no current at balance, and little at off-balance. Its input resistance and sensitivity should be combined to measure a load of 800,000 ohms within about ±0.001 volt sensitivity. A pen lift control is regarded as essential. Catalog information indicates that there are now many manufacturers of X-Y recorders, and among the most popular are those recording on paper scales such as 10×10 inches, with full scale input ranges such as 10, 100, and 1,000 millivolts. FIG. 1 illustrates the use of common graph paper of 8½×11 inch size for office filing, with 7×10 inch rulings, including 20 divisions per inch (not shown in FIG. 1). The voltage axis Y, of 0.020 volt per inch, calls for a 200 mv range. The current axis X, to meet the requirements of an approximately 45° angle of the line recorded through free electrode potential $E_f$, should be adjustable to current ranges such as shown in Table 3 below. The need for ranges beyond this table is seldom encountered in corrosion rate measurement, where interest centers on metal protection. Higher ranges are used in measuring metal pickling rates.

TABLE 3

Current Ranges for X Axis

| Range Nr. | mmA Per Inch | 6 Inch Scale | Range Nr. | mmA Per Inch | 6 Inch Scale | Range Nr. | mmA Per Inch | 6 Inch Scale |
|---|---|---|---|---|---|---|---|---|
| 1 | 0.4 | 2.4 | | | | | | |
| 2 | 1.0 | 6.0 | 5 | 10 | 60 | 8 | 100 | 600 |
| 3 | 2.0 | 12.0 | 6 | 20 | 120 | 9 | 200 | 1,200 |
| 4 | 4.0 | 24.0 | 7 | 40 | 240 | 10 | 400 | 2,400 |

The current ranges of Table 3 can be obtained with a recorder of 10 and 100 millivolt ranges by inserting a network of precision resistors in series with a lead wire carrying the polarizing current $i_p$, with switch-selectable leads to the recorder. The circuit of FIG. 2 shows an alternative means for obtaining range flexibility through calibrations made from the microammeter. A double check of current range is obtained from the microammeter and the recording pen position on the graph. Pen position can be accurately adjusted to change in size of scale rulings of the graph paper, such as from English to Metric units. Possible polarization of the reference electrode by voltage dividing resistors required for range flexibility, is avoided. This means is also more applicable to portable, battery powered instruments, by avoiding the current drain of voltage regulation.

The controls of the potentiometric null circuit used in the X and Y axes of the recorder are illustrated in the nulling circuit of FIG. 2. In the recorder, the arm of potentiometer $R_{12}$ driven by motor $M_2$, is mechanically coupled to an axis movement of the recording pen. The arm of potentiometer $R_{13}$ determines the zero position of the arm of potentiometer $R_{12}$, and is the zero position control in the recorder. The arm of potentiometer $R_{11}$ adjusts the amount of movement of the arm of potentiometer $R_{12}$ produced by a unit of input signal voltage, and in the recorder it is the scale size adjustment. Amplifier A includes a gain control for sensitivity adjustment, an input disconnect switch, and means for then adjusting the amplifier for zero motor drive.

A more precise understanding of device operation is summarized as follows. The error caused by reference electrode position within the potential field produced in the ionic conductor by polarizing current $i_p$ passed between electrodes O and M, is treated as that produced by a reference electrode error resistance $r_{re}$, through which current $i_p$ passes, so that the error voltage is expressed as, $e_v = i_p(r_{re})$. Measurement method adjusts the parallel connection of resistors $R_5$ and $R_6$ to the value, $R_i' = R_i$. Resistors in the nulling correction circuit are selected to make $i_p' = i_p$. The arm setting of $R_5$, which is the value of $K_{ir}$, delivers a fraction of the voltage drop across $R_i'$, for the correction voltage, $e_c = K_{ir}(i_p')(R_i')$. The value of $K_{ir}$ is adjusted to produce the 0.020 volt separation between consecutive transition points of line slope change, to meet the objective of $e_c = e_v$. Accordingly, in the absence of lead wire resistance, $e_v = i_p(r_{re}) = e_c = K_{ir}(i_p')(R_i') = K_{ir}(i_p)(R_i)$, from which $K_{ir} = r_{re}/R_i$, a ratio which is primarily determined from electrode probe design. In the presence of lead wire resistance $R_L$, $e_v = i_p(r_{re} + R_L)$, and $R_i' = R_i + 2R_L$, so that $K_{ir} = (r_{re} + R_L)/(R_i + 2R_L)$. Lead wire resistance is corrected for even when $R_i$ approaches zero.

Measurement Steps

In FIG. 2, measurement of current-potential relationship made with correction for error voltage $e_v$, as illustrated in relationship 1 of FIG. 1, is made through the following steps.

1. Adjustment of $R_5$ and $R_6$ to $R_i'$

The circuit between electrodes O and M is opened by closing switch $S_3$ to position 1: Closing switch $S_1$ to position 1 connects electrodes O and M to device terminals $T_1$ and $T_2$. Terminal $T_5$ is wired to terminal $T_2$, and to one end of potentiometers $R_5$ and $R_6$. By means disclosed in my pending patent application Ser. No. 654,854, filed Feb. 3, 1976, the arm of potentiometer $R_6$ is adjusted to produce the value $R_i'$ across terminals $T_4$ and $T_5$ equal to the value of $R_i$ measured across terminals $T_1$ and $T_2$. If length of lead wires between the terminals of the instrument and the electrodes introduces any significant value of lead wired resistance, the measurement method eliminates the effect of any distributed capacitance between the lead wires, and measures $R_i' = R_i + 2R_L$. The arm of switch $S_7$ is returned to contact with the arm of potentiometer $R_{13}$.

2. Adjustment of $K_{ir}$

In the first measurement made on a corrosion system, the $K_{ir}$ dial is set at an approximate value, such as that found to operate on a previously measured corrosion system judged to be of similar performance. When the $K_{ir}$ value does not produce the 0.020 volt separation between consecutive transition points within the precision selected, alternative techniques are disclosed below.

3. Y Axis Calibration:

The Y axis of the graph is marked in units of 0.020 volt, with the zero position 0.020 volt above the bottom margin to allow for −0.020 volt of anodic polarization downward. The zero position for the current axis is spaced from the left margin by the distance equal to 0.020 volt on the Y axis, to allow for the negative anodic polarization current. Switch $S_1$ is closed to position 2 to disconnect the electrodes and to connect the arm of potentiometer $R_4$ to the plus terminal of the microammeter. Switch $S_8$ is closed to position 1, to disconnect input to the Y axis, to assure that its amplifier is adjusted to then produce no motor drive. Switch $S_3$ is closed to position 2, to connect resistor $R_y$ in series with the microammeter for operation as a millivoltometer of range such as 0.200 volt. Switch $S_8$ is closed to position 3, to connect the negative terminal of the Y axis to the arm of potentiometer $R_2$ and the positive terminal of the Y axis to the positive terminal of the microammeter. Input to the X axis is disconnected in this switching, to assure that its amplifier is adjusted to produce no motor drive. The circuit polarities shown are for recording the cathodic polarization of electrode M in a positive direction along the recorder Y axis. The recording pen, while lifted from the paper, is brought to the zero voltage position on the graph by the zero position control of the Y axis. Switch $S_2$ is closed, and the arm of potentiometer $R_2$ is adjusted to an even voltage on the microammeter, such as 0.016 volt. Pen position on the graph is brought to this microammeter scale reading by adjustment of the Y axis range control. Switch $S_2$ is opened to assure that the pen returns to zero voltage; if not, it is returned by the zero position control and the calibration is repeated with the range control.

4. Null Circuit Adjustment

Switch $S_6$ is closed to activate the null circuit, and power is applied to amplifier A and motor $M_2$. Amplifier A is disconnected from input and balanced for zero motor drive as shown from the position indicating display of the arm of $R_{12}$. Amplifier A is connected to input, and the position of the arm of $R_{13}$ is adjusted if required, to bring the arm of $R_{12}$ to the zero position on said position indicating display.

5. Potential Equalization, M to R

The dial of the Y axis gain control is positioned to zero, Switch $S_3$ is closed to position 1, to disconnect electrode O. Switch $S_1$ is closed to position 1 to connect electrodes M and R. Switch $S_8$ is closed to position 2, to connect the plus pole of the Y axis to reference electrode R, and to connect the minus pole through the voltage equalizing circuit to measured electrode M. Switch $S_5$ is closed. The start of a corrosion system that undergoes acceleration usually produces substantial potential differences between the three electrodes. The gain control of the Y axis is advanced cautiously with this in mind, and the arm of potentiometer $R_8$ is adjusted to return the pen to zero voltage on the graph.

6. Potential Equalization, M to O

Switch $S_8$ in position 2 connects the plus pole of the X axis to the plus pole of the microammeter, and the minus pole to the arm of potentiometer $R_2$. Switch $S_1$ is closed to position 2 to disconnect the electrodes and to connect the arm of potentiometer $R_2$ to the positive pole of the microammeter. Switch $S_3$ is closed to position 3 to connect the microammeter that is at zero current. The X axis range control is set at a position approximately expected for the corrosion system being measured. The pen is positioned to zero current on the graph by the zero control of the X axis. The arm of potentiometer $R_2$ is positioned to zero minutes on the dial scale. Switch $S_1$ is returned to position 1 to connect the electrodes. Switch 2 is closed to connect battery $E_1$. The arm of potentiometer $R_4$ is adjusted to equalize any voltage difference between electrodes M and O, as shown from a zero reading on the microammeter and the pen position. The pen should also show zero voltage on the voltage axis.

7. X Axis Calibration

The arm of potentiometer $R_2$ is advanced to produce about 0.015 volt of cathodic polarization. The range control of the X axis is adjusted to produce approximately at 45° angle on the graph of the current-potential relationship from zero to said cathodic polarization. Observation is made of the pen position on the current axis of the graph and the current reading of the microammeter. If the current is very small, switch $S_3$ is closed to position 4 to increase sensitivity of current measurement and nulling, and pen position is readjusted. If the current is more than about 1/6th the range of the microammeter, switch $S_4$ is closed to a current multiplier resistor $R_{mb}$ and pen position is readjusted. The dial of potentiometer $R_2$ is returned to zero, and from the observations above, the size of current unit is selected from a range in Table 3, to most closely match the value of current per graph division. Switch $S_1$ is closed to position 2 to disconnect the electrodes and to connect the arm of potentiometer $R_4$ to the plus pole of the microammeter. The arm of $R_2$ is adjusted to a microammeter reading of said current range near the maximum for the graph. The arm of potentiometer $R_{11}$ is adjusted for selected nulling range of the arm of $R_{12}$, as shown from the position indicating display. The range control of the X axis is adjusted to bring the pen to the same value of current on the graph as on the microammeter. Switch $S_2$ is opened to assure that the pen returns to zero current; if not, the zero and range controls of the X axis are readjusted.

8. Recording Range Adjustment

Dropping resistor $R_1$ is positioned to minimum DC voltage delivery. Switch $S_1$ is closed to position 1 to connect the electrodes. The arm of potentiometer $R_2$ is adjusted to a dial scale reading of about °20 minutes. Resistor $R_1$ is advanced slowly to produce a current of about 80% of the full scale graph current, as shown from pen position. Frequently, observation of pen traverse during this adjustment can indicate presence or absence of acceleration. The arm of poteniometer $R_2$ is returned to the dial scale reading of 0 minutes, and the corrosion interface of measured electrode M is allowed to approach its undisturbed condition of zero current at potential $E_f$. This generally requires about 5 minutes.

9. Measurement of $i_p$, $e_p$ Relationship

The arm of potentiometer $R_2$ is positioned to a negative dial scale reading of about $-5$ minutes, to start measurement of a line of anodic polarization as shown in FIG. 1. After about one minute to allow for the development of anoidic polarization voltage, motor $M_1$ is turned on with closed clutch drive, and the recording pen is released to the graph paper. In general, the recording is made at least through the $R_2$ dial scale reading of $+20$ minutes, to allow polarization voltage $e_p$ to approach slow rate of change. If the corrosion is unaccelerated, lines of decreasing slope will be recorded, and only the first three lines of cathodic polarization are required, as can be seen during the recording. If the corrosion is accelerated, lines of increasing slope will be recorded initially, and the recording should include at least the first line of decreasing slope that follows, as can be seen during the recording, and as shown in FIG. 1. Motor $M_1$ is turned off, the pen is raised, and the graph paper is removed. When further measurements are not immediately required, the device is turned off by closing all switches to the positions shown in FIG. 2, and releasing the clutch drive to motor $M_1$.

10. Precision Transition Point Determination

According to FIG. 3 of my 3,694,324 patent straight lines are drawn on the recording to bound linear portions of current-potential relationship, thereby determining the transition points with precision. If voltage separation between the consecutive transition points differs from the 0.020 volt separation by more than a selected amount, method of treatment can be selected from one of the alternatives disclosed below.

11. Corrosion Current Measurements:

When 0.020 volt separation between consecutive transition points is obtained within the selected precision, measurement is made according to the 3,694,324 patent of corrosion current $i_A$, and when the corrosion is accelerated, of corrosion currents $i_B$ and $_{xb}$, and if of additional interest for cathodic protection, of potential $e_{xb}$.

When measurement shows the average of the voltage separation between the first three or more transition points differs from 0.020 volt by more than a selected degree of precision such as $\pm 0.002$ volt, a number of alternative techniques are available. In alternative #1, which becomes easy with practice, visual observation is made near the end of the recording of the number of transition points shown, and the value of $K_{ir}$ is adjusted near the end of the recording to produce the polarization voltage of their 0.020 volt separation. This alternative applies to the first measurement made on a corrosion system not measured before, where deviation from the 0.020 volt separation can be comparatively large, and is for the purpose of making a second recording were made at thirteen selected intervals during this corrosion. The corrosion was stopped after 532.5 hours, electrode surfaces were cleaned and lightly pickled to remove oxides, and the electrodes were again weighed.

Table 4 below, includes measurement data obtained when the voltage separations of the transition points indicated the need for adjustment of the $K_{ir}$ value.

TABLE 4

| | | | | Adjustment of $K_{ir}$ Value During Corrosion | | | | | | | |
|---|---|---|---|---|---|---|---|---|---|---|---|
| | | | | Transition Point Voltage Separation | | | | | | | |
| Nr. | HOURS | $R_i'$ | $K_{ir}$ | 27–28 | 28–29 | 29–30 | 30–31 | Average | $i_A$ | $i_B$ | $i_R$ | $i_{xb}$ |
| 3 | 61.0 | 17,900 | .30 | .022 | .020 | .019 | .019 | .020 | 10.1 | 6.0 | 18.2 | 19.5 |
| 6A | 190.7 | 13,800 | .30 | .023 | .024 | .032 | | .026 | 11.4 | 5.8 | 21.8 | 24.0 |
| B | | | .31 | .019 | .020 | .026 | | .022 | 14.0 | 6.5 | 27.1 | 33.0 |
| C | | | .32 | .022 | .020 | .022 | .021 | .021 | 21.1 | 7.7 | 42.9 | 36.5 |
| 9A | 348.3 | 10,700 | .32 | .018 | .023 | .024 | .022 | .022 | 11.0 | 5.3 | 21.1 | 24.0 |
| B | | | .33 | .018 | .019 | .019 | .025 | .020 | 12.0 | 5.5 | 23.0 | 19.0 |
| 12A | 478.0 | 9,300 | .33 | .018 | .026 | .030 | .020 | .024 | 17.3 | 5.8 | 35.9 | 41.0 |
| B | | | .34 | .019 | .020 | .020 | .021 | .020 | 15.0 | 5.7 | 30.3 | 38.0 |
| 13A | 526.5 | 9,300 | .34 | .013 | .018 | .020 | .021 | .019 | 19.9 | 7.5 | 40.3 | 35.0 |
| B | | | .32 | .020 | .023 | .025 | .024 | .023 | 14.0 | 6.2 | 27.4 | 36.5 |
| | | | .33, Averaged measurement, | | | | | | 17.1 | 6.6 | 35.1 | 35.8 | with the adjusted $K_{ir}$ value.

In alternative #2, current lines are drawn through the recorded transition points and adjusted transition points are positioned on these lines to produce the consecutive 0.020 volt separations. Current measurements can be made from these adjusted transition points, or if greater precision is required, a second recording to started with value of $K_{ir}$ adjusted to cause the initial portion of the recording to coincide with adjusted transition point position.

In alternative #3, a plot is made of averaged transition point voltage separation against $K_{ir}$ value, for the purpose guiding selection of $K_{ir}$ value in the plurality of measurements then required.

A first reading of the detail and length of the measurement steps disclosed above can give an impression that operation of the device could be too complex and time consuming. Actual experience in device operation demonstrates that the logical sequence of the steps presents no problem to the operator in effortlessly applying them after the experience of measurements made on two or three corrosion cells. It should be realized that a switch positions can be changed in about two seconds, and that much of the volume in the steps disclosed above is descriptive. The X—Y recording requires about 30 minutes of time lapse. The switching and the measurements made on the recording require about 15 minutes.

The method and device of this invention can be operated through alternatives to the specific circuit switchings shown, and with minor modifications of the measurement steps disclosed, provided that the quality of the measurements obtained furnishes useful information.

EXAMPLE 1: Iron In Quiescent Distilled Water

Although some corrosives that contain in part nonionizing dissolved substances have a higher resistivity than distilled water, this example with single distilled water is regarded to be more closely related to industrial experience.

Six weighed electrodes of C-1018 steel, including the three electrode corrosion probe described above, were immersed in four liters of single distilled water exposed to the atmosphere at room temperature and without stirring. Measurements by the device of this invention With this corrosion system, $K_{ir}$ value ranged from 0.30 to 0.34, and adjustment to the 0.020 volt transition point separation was maintained within the precision of ±0.001 volt on the averaged value. Illustration is made in a number of instances, of the effect of a change in $K_{ir}$ of 0.01 in arriving at the required adjusted value. Changes in value of $i_A$, $_B$, and $_{xb}$ with change in $K_{ir}$ value are in accord with what would be expected from FIG. 1. The value of $R_i'$ at the start of the corrosion was 31,400 ohms. The data of Table 4 illustrates the substantial independence of $K_{ir}$ value to a decrease of $R_i'$ value −48 %.

In general, it would be expected that the build-up of adherent corrosion products would in effect introduce additional resistance to the $r_{re}$ value, which would require an increase in the $K_{ir}'$ value. In this corrosion of iron by distilled water, flocculent corrosion products did not adhere significantly to electrode surfaces and black oxide was very thin. In the corrosion of iron in lake water, the formation of a dense adherent calcium carbonate scale over cathodic areas, together with black oxide formation on some anodic areas, was accompanied by a doubling of the $R_i'$ value, and $K_{ir}$ increased up to 0.6. However, the accuracy of corrosion rate measurement made by $i_R$ and $i_{xb}$ was not impaired.

During the duration of this corrosion in distilled water, the corrosion rates measured by $i_R$ and $_{xb}$ passed through three oscillations of smooth curvature and of substantial magnitude, which are only in part reflected in the data of Table 4. The accuracy of correction for the ionic conductor IR drop between measured and reference electrodes is evidenced from the metal loss measurements of Table 5.

TABLE 5

| | Accuracy of IR Drop Correction | |
|---|---|---|
| Nr. | Metal Loss Measurement | Milligrams |
| 1 | Integration of $i_R$-time relationship to mg.-time | 15.3 |
| 2 | Integration of $i_{xb}$-time relationship to mg.-time | 15.1 |
| 3 | Weight loss, electrode O | 16.8 |
| 4 | Weight loss, electrode M | 13.8 |
| 5 | Weight loss, average of electrodes O and M | 15.3 |
| 6 | Weight loss, unmeasured control electrode | 15.6 |

All of the measurements are in agreement within the ±5% precisions within which the two methos operate.

The measurement method of this invention slightly increased weight loss on electrode O operated during the measurement as an anode, and slightly decreases weight loss on electrode M operated substantially as a cathode during measurement, but the average of the two is in close agreement with the other measurements. A high order or precision in IR correction through the method and device of this invention is thereby demonstrated.

FIG. 3

FIG. 3 shows an alternative and simplified embodiment of the device, in which the servo nulling means of FIG. 2 for correcting error voltage $e_v = i_p(r_{re})$, is replaced by a potentiometer delivering correction voltage from the DC voltage applied to the opposed and measured electrodes during the polarization measurement.

In FIG. 3, the circuitry for applying the DC voltage $e_{om}$ to electrodes O and M, and for measuring and recording the polarizing current $i_p$ and the polarization voltage $e_p$, is the same as that in FIG. 2.

In FIG. 3, a potentiometer $R_{14}$ is connected across instrument terminals $T_1$ and $T_2$, and is energized by the DC voltage $e_{om}$ applied to electrodes O and M in measuring the range of $i_p$, $e_p$ relationship. Correction for the error voltage $e_v$, is made by positioning the arm of potentiometer $R_{14}$ the value of $K_{ir}$ that produces the 0.020 volt separation between transition points of line slope change, as disclosed above. Switch $S_9$ can disconnect potentiometer $R_{14}$ and connect potentiometer $R_{15}$ for measuring higher ranges of polarizing current.

The ohmic value for potentiometer $R_{14}$ is determined from the DC voltage $e_{om}$ applied across electrodes O and M at the polarizing current $i_{xb} = ]i_R$, and from the percent of positive error to be tolerated in $i_R$ measurement from the current drawn by $R_{14}$ when applied across voltage $e_{om}$. The largest ohmic value of $R_{14}$ is required for the smallest $i_R$ range to be measured, where the current passed through it must also be the smallest. Range 1 of Table 1 is taken as a usual limit for the device of FIG. 3, and from this table, $i_R = 1$ mmA, $R_i = 50,000$ ohms.

The voltage $e_{om}$ is the sum of the series voltages comprising the anodic polarization voltage of electrode O at current $i_R$, the ionic conductor resistance drop of $i_R(R_i) = (1 \times 10^{31\ 6})$ (50,000) = 0.50 volt, and the cathodic polarization voltage of electrode M at current $i_R$. The polarization voltages are determined through proportionalities of the Interface Electrode System shown in FIG. 2 of said 3,694,324 patent, on the assumption that the value of $i_R = 1.0$ mmA is produced by $i_A = 0.5$, $i_B = 0.2$ mmA, for the $i_A/i_B$ ratio of 2.5 as follows.

The cathodic polarization voltage $e_M$ of electrode M is determined from FIG. 2 of said patent, as follows. In said figure, $i_B$ is shown as 10 current units. For the above $i_A/i_B$ ratio of 2.5, $i_A$ in said figure is 25 units, corresponding to point 10' which is in turn based upon the polarization at point 10, of about 0.045 volt on the potential axis. This potential corresponds to the potential $E_f$ at which the corrosion occurs undisturbed. To polarize cathodically to $i_{xb} = i_R$ requires that the potential be increased to 0.090 volt in said figure. Then, $e_M = 0.909 - 0.045 = 0.045$ volt.

The anodic polarization voltage $e_O$ of electrode O, is determined as follows from FIG. 2 of said patent. Point 10, shown at 45 current units, is regarded to be at potential $E_f$ in this determination. The cathodic current to polarize it to potential 0.090 volt is this 45 unit value of current. An equal anodic polarizing current of 45 units beyond point 10 then determines the potential at which electrol O is polarized. FIG. 2 is easily extrapolated to 90 current units, to define the potential of about 0.025 volt, from which the anodic polarization voltage is, $e_O = 0.045 - 0.025 = 0.020$ volt.

The ohmic value for $R_{14}$ is then calculated as follows. From the calculations above $e_{om} = e_o + i_R(R_i) + e_M = 0.045 + 0.020 = 0.115$ volt. If $R_{14}$ introduces a +5% error in $i_R$, the current through it is (1.0) (0.05) = 0.05 mmA. Then, $R_{14} = e/i = 0.115/(0.05 \times 10^{-6}) = 2,300,000$ ohms.

This large ohmic value for $R_{14}$ means that the Y axis of the recorder must operate with required sensitivity from a load of high ohmic value. The largest ohmic value of load to the Y axis would be when the arm of $R_{14}$ is at the middle position. The resistance of the DC voltage delivery system is so small compared to $R_{14}$, that it can be regarded as a short-circuit across $R_{14}$. The mid-arm position of $R_{14}$ then represents a load of 2.3/2 = 1.15 megohms to the Y axis. Expensive recorders are available to operate at this large load resistance, but a more usual performance, stated above, is a sensitivity of +0.001 volt at 800,000 ohms of load. $R_{14}$ could then be 1.6 megohms, or in commercially available size, 1.5 megohms. The current then drawn by $R_{14}$ would be $0.115/(1.5 \times 10^{+6}) = 0.077$ mmA, representing an error of +8%.

In Range 2 of Table 1, $i_R = 10$ mmA and $R_i = 5,000$ ohms, and so $(i_R)(R_i)$ remains unchanged. Voltage $e_{om}$ then also remains unchanged. A second resistor $R_{15}$ can be used for this range and for the higher current ranges, through the use of switch $S_9$. If $R_{15}$ is taken as 500,000 ohms, the current it draws is $0.115/(0.5 \times 10^{+6}) = 0.23$ mmA, and the error is +2.3%, while the load resistance to the Y axis is only 250,000 ohms. At Range 3 of Table 1, where $i_R$ is 100 mmA, the error current would be only 300.23%.

In the device of FIG. 3, the arms of potentiometers $R_{14}$ and $R_{15}$ are calibrated in $K_{ir}$ units from 0.00 to 1.00, starting from the end to which they are connected to measured electrode M. Correction voltage is $e_c = K_{ir}'(e_{om})$, from which $K_{ir}' = e_c/e_{om}$. Since $e_c$ is adjusted for $e_c = e_v = i_p(r_{re})$, while $e_{om} = i_p(r_{po} + R_i + r_{pm})$, then in absence of lead wire resistance, $K_{ir} = r_{re}/(r_{po} + R_i + r_{pm})$, and in the presence and lead wire resistance, $K_{ir}' = (r_{re} + R_L)/(r_{po} + R_i + r_{pm} + 2R_L)$.

While in FIG. 2 it was shown that $K_{ir} = r_{re}/R_i$ is primarily determined by probe design and operates through a value substantially independent of change in $R_i$ and corrosion rate during progress of the corrosion, $K_{ir}'$ differs in not being independent of change in $R_i$ value or of change in corrosion rate. Also, during the X-Y recording, $K_{ir}'$ undergoes small variations as polarizing current $i_p$ is increased from zero through $i_{xb}$, consequent to the variations in $r_{po}$ and $r_{pm}$ with current density according to the Interface Electrode System. However, the amount of error thereby introduced into the measurement of $i_A$, $i_B$ and $i_{xb}$, can be shown through additional calculations to be of relatively minor consequence, as can be more easily understood by noting the relatively small deviations of relationship 1 of FIG. 1 from an averaging straight line superimposed upon it.

One comparison of the numeric values for $K_{ir}$ and $K_{ir}'$ is based on the calculations above for Range 1 of Table 1. In FIG. 2, when $K_{ir}$ is taken as 0.3, $e_c = (0.3)(1 \times 10^{-6})(50,000) = 0.0150$ volt. In FIG. 3, where $K_{ir}$ $= e_c/e_{om}$, the calculations above gave $e_{om} = 0.115$ volt. Then, $K_{ir}' = 0.0150/0.115 = 0.130$.

With the device of FIG. 2, demonstration was made through Example 1, of the substantial independence of $K_{ir}$ to a decrease in $R_i$ of 48%. With the device of FIG. 3, the effect of decreasing $R_i$ by 50% in the calculations above, shows that when $R_i = 25,000$ ohms, $e_c = 0.0150/2 = 0.0075$ volt, and $e_{om} = 0.115 - i_p(25,000) = 0.090$ volt, with the consequence that $K_{ir}' = 0.0075/0.090 = 0.083$.

Figure 4:
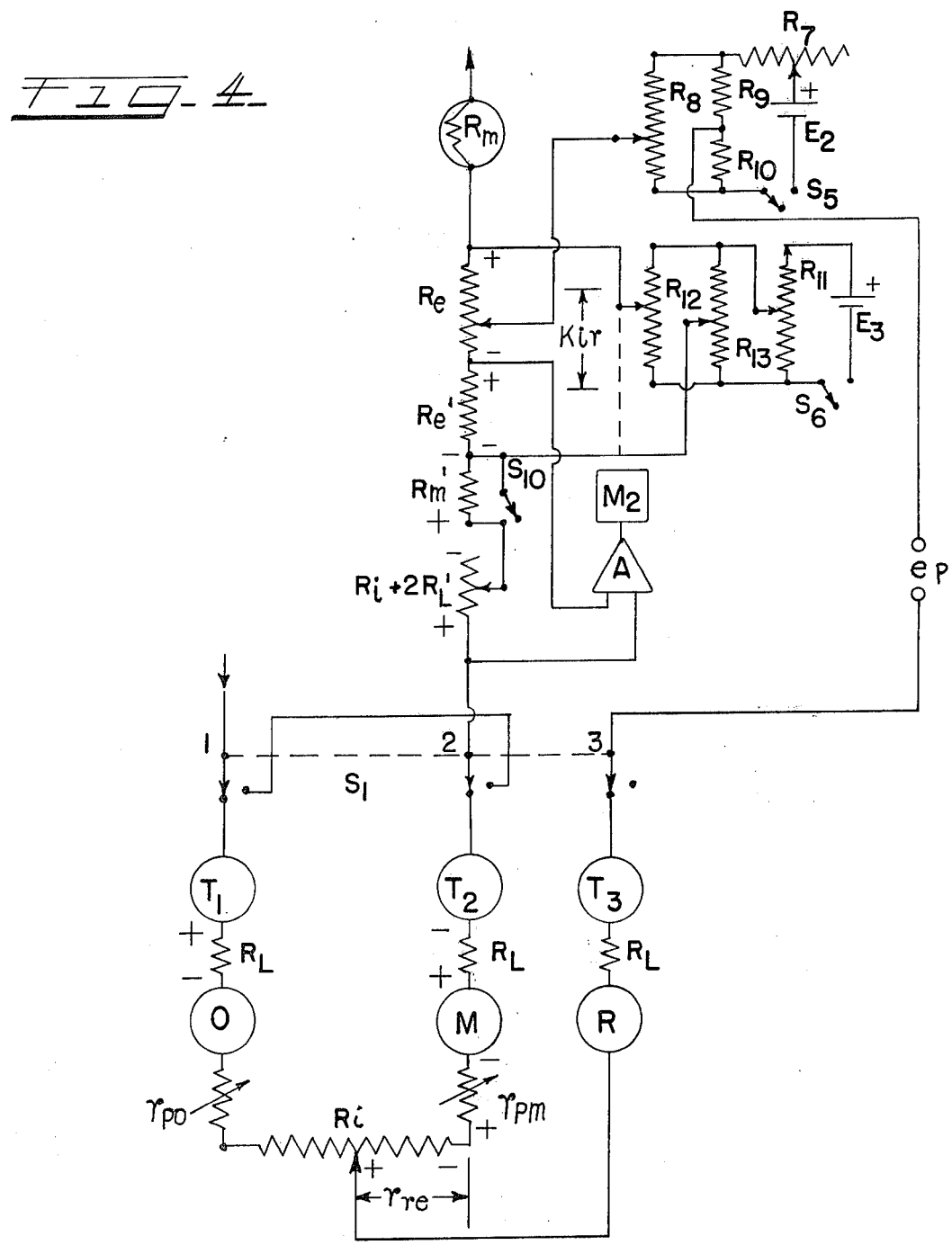
FIG. 4 illustrates circuitry for a device combining corrosion current measurement made on duplicated measured electrodes with measurement made on one measured electrode.

FIG. 4 is a simplified circuit diagram showing correction for ionic conductor resistance $R_i$ and lead wire resistance $R_L$ when applied to a device that combines operation through two measured electrodes according to my pending U.S. Patent application Ser. No. 654,854 now U.S. Pat. No. 4,060,461 with operation through the nulling circuit of FIG. 2 herewith. The detail of switching between the two forms of DC voltage delivery required in these two measurement method alternatives for producing polarizing current $i_p$, is omitted to simplify the showing of FIG. 4, and such detail is regarded to be within the skill of the art.

In either mode of operation, and at the start of the measurement, the resistor connected to terminal $T_2$ is adjusted to $R_i' + 2R_L' = R_1 + 2R_L$, as disclosed above. Resistor $R_e'$ is selected to exactly equal the full winding resistance of potentiometer $R_e$. With switch $S_6$ closed, amplifier A drives motor $M_2$ connected to the arm of potentiometer $R_{12}$, to maintain zero voltage at the amplifier input.

When the device of FIG. 4 is operated through measurements made on duplicated measured electrodes, O and M, switch $S_{10}$ is in th open position and resistor $R_m'$ equals meter resistance $R_m$. With a polarizing current $i_p$ flowing in the direction indicated, the voltage drop across resistors $(R_i' + 2R_L)$ and $R_m'$ is exactly opposed by the voltage rise across resistor $R_e'$. An equal voltage rise across potentiometer $R_e$ adds voltage to correct for the voltage drops of ionic conductor and lead wire resistances, and for meter resistance. Polarizing current $i_p$ can be measured from the voltage drop across meter $R_m$ and recorded on the Y axis. The X axis can alternatively measure cathodic polarizing current $i_x$ passed to each measured electrode during measurement of accelerated corrosion, or can be operated as a time axis from a voltage delivered at a selected constant rate of increase.

When the device of FIG. 4 is operated through measurements made with one measured electrode, switch $S_{10}$ is closed to cancel correction for voltage loss through the microammeter. Switch $S_5$ is closed, and as in FIG. 2, the arm of potentiometer $R_8$ is adjusted to equalize difference in free electrode potential between measured electrode M and reference electrode R. With a polarizing current $i_p$ flowing in the direction indicated, the voltage drop across resistor $R_i' + 2R_L'$ is exactly opposed by the voltage rise across resistor $R_e'$. The voltage rise across potentiometer $R_e$ is then equal to that of the parallel connection in FIG. 2 of resistors $R_5$ and $R_6$, the value, $(i_p)(R_i' + 2R_L')$. The arm of potentiometer $R_e$ is adjusted to the value for $K_{ir}$ as in FIG. 2.

Throughout the scope of corrosion interface composition and corrosive environment measured to date, some abnormal behavior and performance have been encountered. In my earlier patents, instances were mentioned where anodic valence through which the corrosion current operates differs from corrosion product valence, and the corrosion current-time relationship correlates with weight loss measurement when integrated to quantity-time relationship through a different whole-number anodic valence.

Another abnormality is more frequently encountered, as with the corrosion system of Example 1. When the corrosion current is measured with duplicated measured electrodes, the applied DC voltage with the added voltage correction for $i_p R_i$, is delivered at a constant rate of increase during a time of about two minutes, and the current $i_A$ then holds for about 40 seconds. During the next fifteen to twenty minutes the current then decreases to approach an equilibrium value of about 60% of the initial value. Upon then removing the applied DC voltage and short-circuiting the duplicated electrodes, a reversed current peak is observed from which the current decreases during the next fifteen to twenty minutes in a return to the initial free electrode potential. It is found that the value of current separation between the reversed current peak and the equilibrium value approached during the DC voltage application, is substantially equal to the $i_A$ value produced initially. Consequently current $i_A$ can be measured at the initial peak value, to save the time otherwise required for its approach toward an equilibrium value. The phenomena is regarded to be cancelled during the cathodic polarization applied to both electrodes during measurement of current $i_B$.

With measurement made on one measured electrode with a reference electrode according to the method and device of this invention, the phenomena does not effect the cathodic polarization that produces accurate measurement, but decreases the anodic polarization to an extent causing the slope of the anodic current-potential relationship to approach a horizontal line. The technique for handling this phenomena is based upon the finding that the free electrode potential at zero polarizing current normally falls within a mid-way zone on the line between the first transition point of cathodic polarization and the first transition point of anodic polarization. Although the portion of this line that extends into anodic polarization at the greatly reduced slope can no longer measure $i_A$, the portion that is included in the cathodic polarization does accurately measure $i_A$.

In measuring the performance of a single measured electrode, the method and device of this invention produce information otherwise not obtainable. It also has the advantage of a more pictorial showing of corrosion mechanism in its recorded measurement.

The device of FIG. 2 is superior for operations of research and development, where the measured corrosion system may be selected anywhere within a wide scope of corrosion interface composition and environment.

In the field, where interest usually centers on the control of a specific process within prescribed limits of variation, the device of FIG. 3, through elimination of the nulling system, offers less weight, less power consumption on battery operation, fewer controls and steps, and lower price. Although I consider the device of FIG. 2 to be the preferred embodiment, the device of FIG. 3 may alternatively be the preferred embodiment for applications with narrower limits of variation.

It will be understood that various changes and modifications may be made without departing from the spirit of the invention as defined in the following claims and equivalents thereof.

| GLOSSARY OF SYMBOLS & TERMS | | | |
|---|---|---|---|
| SYMBOL | MEANING | MEASURED | RELATIONSHIPS |
| $R_i$ | Ionic conductor resistance between electrodes O and M | | |
| $R_i'$ | Value measured between terminals $T_1$ and $T_2$ by ac voltage | Yes | $R_i' = R_i$; When lead wire resistance $R_L$ is present, $R_i' = R_i + 2R_L$ |
| Effective parallel of $R_5$ and $R_6$ | Adjusted to $R_i'$ | Yes | |
| $i_p$ | DC current polarizing measured electrode M cathodically | Yes | |
| $E_f$ | Electrode potential, unpolarized, (free) | yes | |
| $e_m$ | Potential of polarized electrode | yes | |
| $e_p$ | Polarization voltage produced by $i_p$ | yes, $e_p = e_m - E_f$ on graph | |
| $r_{re}$ | An equivalent resistance | | |
| $e_v$ | Error voltage of ionic conductor IR drop between measured and reference electrodes | | $e_v = i_p(r_{re})$ |
| $i_p'$ | Current passed through $R_5$ and $R_6$ by nulling circuit | | Through selection of circuit values, $i_p' = i_p$ |
| $K_{ir}$ | Dial position of arm of $R_5$ on scale of 0 to 1.0 | | |
| $e_v$ | Correction voltage opposing $e_v$ | | $e_v = K_{ir}(i_p')(R_i')$ |
| 0.020 volt separation between transition points | $e_v = e_v$ | Yes | Then: $i_p(r_{re}) = i_p(K_{ir})(R_1')$ Since, $i_p' = i_p$ and $R_i' = R_i$, then, $r_{re} = K_{ir}(R_i)$, or $K_{ir} = r_{re}/R_i$ With $R_L$, $r_{re} + R_L = K_{ir}(R_i + 2R_L)$; $K_{ir} = \dfrac{r_{re} + R_L}{R_i + 2R_L}$ |
| RL | Resistance of lead wire | | |

| SYMBOL | MEANING | RELATIONSHIPS |
|---|---|---|
| $i_R = 1$ mmA, $R_i = 50{,}000$ ohms $i_A = 0.5$ mmA, $i_B = 0.2$ mmA | From Table 1, smallest current range to be measured by Simplified Method Values assigned to represent $i_R = 1 = 2.4(0.2) - 0.2$ | |
| $R_{14}$ | Potentiometer across terminals $T_1$ and $T_2$ | Ohmic value for $R_{14} = ?$ |
| $e_{om}$ | DC voltage applied to electrodes O and M to polarize by $i_p = i_{xb} = i_R$ | |
| 5% of $i_R$ | Allowable current through $R_{14}$ | $R_{14} = e_{om}/(0.05)(i_R)$ |
| $e_M$ | Cathodic polarization voltage of M by $i_R$ | |
| $e_O$ | Anodic polarization voltage of O by $i_R$ Values of $e_M$ and $e_O$ determined through proportionalities of FIG. 2 of U.S. Pat. No. 3,694,324, in steps shown to right. | $e_{om} = e_M + i_R(R_i) + e_O$ 1: From above, $i_A/i_B = 0.05/0.2 = 2.5$; 2: In FIG. 2 of Pat., $i_B = 10$ current units; 3: For $i_A/i_B = 2.5$, $i_A$ in FIG. 2 of Pat. is then 25 current units; 4: Horizontal line at $i_A = 25$ intersects line $i_R = 2.4(i_A) - i_B$ at substantially point 10'; 5: Point 10' was located from $i_A$ measured when $E_f$ is at point 10; (the $E_{fc} - C_c$ curve of Pat. FIG. 1 passes through point 10); 6: In Pat. FIG. 2, $i_{xb} = i_R$ is measured when M is cathodically polarized |

-continued
GLOSSARY OF SYMBOLS & TERMS

| | | |
|---|---|---|
| $e_M = 0.045$ v. Shown at right | | from point 10 to $E_{fa} = 0.09$ v; point 10 is at 0.045 v; accordingly, $e_m = 0.090 - 0.045 = 0.045$ |
| | | 7: Point 10 is at 45 current units on the abscissa axis; $-45$ current units are required to polarize M cathodically to $E_{fa}$; |
| | | 8: Then, anode O is polarized $+45$ current units from point 10, to 90 current unit |
| | | 9: The $E_{fa} - A$ relationship can be extrapolated linearly to potential $P_{c4}$; |
| $e_O = 0.020$ v. Shown at right | | 10: 90 current units intercepts said extrapolated line at substantially 0.025 v; $e_O = 0.045 - 0.025 = 0.020$ v; |
| $e_{om} = 0.115$ v. Shown at right | | 11: And so, $e_{om} = 0.045 + (1 \times 10^{-6})(5 \times 10^4) + 0.020 = 0.115$ v; |
| $R_{14} = 2.3$ meg. Shown at right | | 12: By substitution, $R_{14} = 0.115/(0.05 \times 10^{-6}) = 2,300,000$ ohms. |
| $K_{ir}'$ | Dial position of arm of $R_{14}$ on scale of 0 to 1.0 | $K_{ir}' = r_{re}/(r_{po} + 2R_i + r_{pm})$ |
| $R_L$ | Resistance of lead wire | $K_{ir}' = \dfrac{r_{re} + R_L}{r_{po} + R_i + r_{pm} + 2R_L}$ |

I claim:

1. In the measurement of corrosion currents of an Interface Electrode System through measurement of a range of current-potential relationships on a system including a nongaseous ionic conductor in which are immersed a measured electrode, an opposed electrode, and a reference electrode wherein the reference electrode is spaced from said measured electrode, the method of correcting for the sum of the IR voltage drops of ionic conduction between said measured and reference electrodes and of electronic conduction in a lead wire between a measuring device and the measured electrode, comprising the steps of:

establishing an IR drop across a potentiometer by passing a DC correction current therethrough, said IR drop having a voltage greater than the sum of the IR drops to be corrected for;

maintaining said correction current at a value proportional to a DC polarizing current of said measured current-potential relationship, and in a direction of flow fixed with relation to the direction of flow of said DC polarizing current;

providing one end and an arm of said potentiometer in series with a potential measuring circuit between said measured and reference electrodes, and in polarity to oppose the polarity of said IR drops; and adjusting the arm of said potentiometer to deliver that value of correction voltage that produces approximately 0.02 volt separations between transition points of line slope change in an X-Y recording of said measured range of current-potential relationships.

2. The method of claim 1 further comprising the steps of;

connecting said potentiometer across a pair of device terminals leading to said opposed and measured electrodes; and delivering a correction voltage at the arm of said potentiometer to the electrode potential measuring circuit.

3. The method of claim 1 further comprising the steps of;

connecting one end of said potentiometer to said measured electrode;

connecting a first nulling resistor in series with said DC polarizing current such that one end of said first nulling resistor is connected to said measured electrode;

connecting a second nulling resistor in series with said correction current such that one end of said second nulling resistor is connected to said measured electrode;

using a servo system to null the difference in IR drops across said nulling resistors to control the polarity and value of said correction current; and using the arm of said potentiometer to deliver a correction voltage to the electrode potential measuring circuit.

4. The method of claim 3 further comprising the steps of;

connecting a second potentiometer at one end to a device terminal leading to said measured electrode such that the arm of said second potentiometer is in parallel connection with the total resistance of said first potentiometer;

selecting the ohmic values of said first and second potentiometers to produce a maximum parallel resistance equal to the largest sum of ionic conductor resistance and lead wire resistance between the device terminals leading to said opposed and measured electrodes in the range of corrosion systems to be measured; and adjusting the arm of said second potentiometer to produce a parallel resistance equal to the sum of ionic conductor resistance and lead wire resistance which are measured between the device terminals leading to said opposed and measured electrodes, before measuring said range of current-potential relationships.

5. The method of claim 4 further comprising the step of selecting said first nulling resistor to be the same ohmic value as said second nulling resistor.

6. The method of claim 4, comprising:
applying correction for distributed capacitance between lead wires connecting measurement device to electrodes in the measurement of lead wire resistance $2R_L$ and of ionic conductor resistance $R_i$, thereby maintaining accuracy of corrosion current measurement as length of lead wires is increased.

7. The method of claim 1, further comprising the steps of:
connecting one end of said potentiometer to a lead wire to pass polarizing current to said measured electrode;
connecting the other end of said potentiometer to one end of a fixed resistor of ohmic value selected to equal the total resistance of said potentiometer;
connecting the other end of said fixed resistor to the arm of a second potentiometer;
connecting one end of said second potentiometer to a device terminal for connection to said measured electrode;
establishing a DC voltage delivery circuit in which DC voltage is delivered between the arm of a voltage delivery potentiometer and the arm of a parallel connected zero adjust potentiometer;
connecting the arm of said voltage delivery potentiometer to the point of connection of said lead wire to said potentiometer;
connecting the arm of said zero adjust potentiometer to the point of connection of said fixed resistor to the arm of said second potentiometer;
connecting one input lead of a servo nulling system to said device terminal;
connecting the other input lead of said servo nulling system to the point of connection of said fixed resistor to said potentiometer;
connecting the output motor drive of said servo nulling system to the arm of said voltage delivery potentiometer with direction of drive oriented to circuit polarities to produce the voltage nulling;
connecting the arm of said potentiometer to one lead to the potential measuring circuit; and
using the arm of said potentiometer to deliver correction voltage.

8. The method of claim 7, further comprising the steps of:
selecting the ohmic value of said second potentiometer to produce maximum resistance equal to the largest sum of ionic conductor resistance and lead wire resistance between device terminals leading to said opposed and measured electrodes in the range of corrosion systems to be measured; and
adjusting the arm of said second potentiometer to a value of resistance equal to the sum of ionic conductor resistance and lead wire resistance which are measured between device terminals leading to said opposed and measured electrodes, before measuring said range of current-potential relationships.

9. The method of claim 1, including:
positioning cylindrical electrodes with their major axes in parallel relationship;
holding said electrodes within the ionic conductor by insulators of the same diameter as the electrodes;
shielding top and bottom ends of said electrodes by means substantially eliminating crevice corrosion at the shielded boundary;
and locating the electrode assembly within the ionic conductor at a separation distance from the liquid surface and walls containing the liquid to minimize interference with the field of current conduction between the electrodes,
whereby accuracy of corrosion current measurement is maintained as resistivity of ionic conductor is increased, and in the presence of accelerated corrosion.

10. In apparatus for measuring corrosion currents of an Interface Electrode System through measurement of a range of current-potential relationships on a system including a nongaseous ionic conductor in which are immersed a measured electrode, an opposed electrode, and a reference electrode wherein the reference electrode is spaced from said measured electrode, improvement through means to correct for the sum of IR voltage drops of ionic conduction between said measured and reference electrodes and of electrode conduction in a lead wire between a measuring device and the measured electrode, said apparatus comprising:
means for establishing an IR drop across a potentiometer by passing a DC correction current therethrough, said IR drop having a voltage greater than the sum of the IR drops to be corrected for;
means for maintaining said correction current at a value proportional to a DC polarizing current of said measured current-potential relationship, and in a direction of flow fixed with the relation to the directional flow of said DC polarizing current;
one end and an arm of said potentiometer in series with a potential measuring circuit between said measured and reference electrodes, and in polarity to oppose the polarity of said IR drops; and
means for adjusting the arm of said potentiometer to deliver that value of correction voltage that produces approximate ly 0.02 volt separations between transition points of line scope change in an X-Y recording of said measured range of current-potential relationships 11. The apparatus of claim 10 wherein said potentiometer is connected across a pair of device terminals leading to said opposed and measured electrodes; and wherein the apparatus further comprises means for delivering a correction voltage at the arm of said potentiometer to the electrode potential measuring circuit.

12. The apparatus of claim 10 wherein one end of said potentiometer is connected to said measured electrode;
a first nulling resistor is connected in series with said DC polarizing current such that one end of said nulling resistor is connected to said measured electrode;
a second nulling resistor is connected in series with said correction current such that one end of said second nulling resistor is connected to said measured electrode;
servo system means to null the difference in IR drops across the nulling resistors to control the polarity and value of said correction current; and
the arm of said potentiometer delivers a correction voltage to the electrode potential measuring circuit.

13. The apparatus of claim 12 further comprising:
a second potentiometer with one end connected to a device terminal leading to said measured electrode such that an arm of said second potentiometer is in parallel connection with the total resistance of said first potentiometer;
the ohmic values of said first and second potentiometers are selected to produce a maximum parallel resistance equal to the largest sum of ionic conductor resistance and leadwire resistance between the device terminals leading to said opposed and measured electrode in the range of corrosion systems to be measured; and the arm of said second potentiometer is adjustable to produce a parallel resistance equal to the sum of ionic conductor resistance and lead wire resistance which are measurable between the device terminals leading to said opposed electrodes, thereby preparing said apparatus for measuring the range of current-potential relationships.

14. The apparatus of claim 13 wherein said first nulling resistor is the same ohmic resistance value as said second nulling resistor.

15. The apparatus of claim 6, wherein:

said potentiometer is connected at one end to a lead wire to pass polarizing current to said measured electrode;

a fixed resistor of ohmic value selected to equal the total resistance of said potentiometer is connected at one end to the other end of said potentiometer;

a second potentiometer is connected through its arm to the other end of said fixed resistor;

the device terminal for connection to said measured electrode is connected to one end of said second potentiometer;

means for DC voltage delivery including a voltage delivery potentiometer and a zero adjust potentiometer connected in parallel with the arm of said voltage delivery potentiometer connected to the point of connection of said lead wire to said potentiometer;

the arm of said zero adjust potentiometer connected to the point of connection of said fixed resistor to the arm of said second potentiometer;

a servo nulling system with one input lead connected to said device terminal;

the other input lead of said servo nulling system connected to the point of connection of said fixed resistor to said potentiometer;

the output motor drive of said servo nulling system connected to the arm of said voltage delivery potentiometer with direction of drive oriented to circuit polarities to produce the voltage nulling; and the arm of said potentiometer delivering a correction voltage to the electrode potential measuring circuit.

16. The apparatus of claim 15, further comprising:

said second potentiometer of ohmic value selected to produce maximum resistance equal to the largest sum of ionic conductor resistance and lead wire resistance between device terminals leading to said opposed and measured electrodes in the range of corrosion systems to be measured;

the arm of said second potentiometer adjustable to a resistance value equal to the sum of ionic conductor resistance and lead wire resistance which are measurable between device terminals leading to said measured and opposed electrodes; and thereby preparing said apparatus for measuring the range of current-potential relationships.

17. The device of claim 10, including cylindrical electrodes positioned with their major axes in parallel relationship;

means holding said electrodes within the ionic conductor by insulators of the same diameter as the electrodes;

means shielding top and bottom ends of said electrodes by means substantially eliminating crevice corrosion at the shielded boundary;

and means locatng the electrode assembly within the ionic conductor at a separation distance from the liquid surface and walls containing the liquid to minimize interference with the field of current conduction between the electrodes, whereby accuracy of corrosion current measurement is maintained as resistivity of ionic conductor is increased, and in the presence of accelerated corrosion.

18. In a device for measuring corrosion currents of the Interface Electrode System through measurement of initial range of current-potential relationship made on a system including a non-gaseous ionic conductor in which is immersed a measured electrode, an opposed electrode, and a reference electrode in the form of an electrode spaced from said measured electrode the improvement comprising:

means for DC voltage delivery to said measured and opposed electrodes including a source of variable DC voltage connected across first and second potentiometers;

a motor connected to the arm of said first potentiometer through a releasable clutch mechanism and gear train adapted to drive the arm of said first potentiometer across its resistor from positive to negative polarity through a time lapse of about 30 minutes, with the arm of said first potentiometer connected to said measured electrode and the arm of said second potentiometer connected to said opposed electrode;

means for polarizing current measurement comprising a microammeter connected in series with the polarizing current, and the X axis input of an X-Y recorder connected across said microammeter;

an error correcting potentiometer connected at one end to said measured electrode;

means for polarization voltage measurement including one lead from the Y axis input of said X-Y recorder connected to said reference electrode, and the other lead connected through a free electrode potential equalizing circuit to the arm of said error correcting potentiometer;

means for passing a correction current through said error correcting potentiometer, proportional to said polarizing current and in direction to oppose the polarization voltage produced on said measured electrode; and whereby the voltage separation between consecutive transition points in the recorded current-potential relationship is made substantially equal to 0.020 volt by the adjusted position of the arm of said error correcting potentiometer.

19. The device of claim 18, in which the means for passing said correction current includes:

a voltage drop across a resistor in series with the DC current polarizing the measured electrode;

a voltage drop across a resistor in series with an error correction circuit that includes the series connection of said error correcting potentiometer; and means for continuously nulling said two voltage drops through means controlling the DC current in said error correction circuit.

20. The device of claim 19, in which the ohmic values of the two resistors producing the nulled voltage drops are made equal and in which the error correcting potentiometer comprises:
- a resistance adjustment potentiometer connected at one end to said measured electrode;
- a correction voltage potentiometer connected at one end to said measured electrode and connected at the other end to the arm of said resistance adjustment potentiometer, and connection of the arm of said resistance adjustment potentiometer to the lead wire passing said correction current to said measured electrode;
- whereby the ohmic value of the error correcting potentiometer is adjusted to equal the sum of the measured value of ionic conductor resistance between the measured and opposed electrodes and the lead wire resistance between the device terminals to said electrodes through adjustment of the arm of said resistance adjustment potentiometer; and
- the correction voltage is delivered from the arm of said correction voltage potentiometer.

21. The device of claim 18, in which the means for passing said correction current includes connection of the other end of said error correcting potentiometer to said opposed electrode.

22. The device of claim 11, in which the means for passing said correction current includes:
- one end of a resistance correction potentiometer connected directly to the measured electrode;
- the arm of said resistance correction potentiometer connected to one end of a resistor of selected ohmic value;
- the other end of said resistor of selected ohmic value connected to one end of said error correcting potentiometer;
- the resistor of said error correcting potentiometer of the same selected ohmic value;
- the other end of said error correcting potentiometer connected to the lead wire passing polarizing current to said measured electrode; and
- a continuous nulling circuit with one input lead connected to said measured electrode, with the other input lead connected to the junction of said selected resistor and said error correcting potentiometer, and with output adapted to drive the arm of a power potentiometer delivering DC voltage of reversible polarity to the series connection of said selected resistor and said correction potentiometer.

23. The device of claim 22, in which the value of resistance between the arm of said resistance correction potentiometer and said measured electrode is equal to the sum of the measured value of ionic conductor resistance
- between said measured and opposed electrodes and the lead wire resistance
- between the device terminals and said electrodes.

24. The device of claim 23, including means for:
- applying correction for distributed capacitance between lead wires connecting measurement device to electrodes in the measurement of lead wire resistance $2R_L$ and of ionic conductor resistance $R_i$,
- thereby maintaining accuracy of corrosion current measurement as length of lead wires is increased.

* * * * *

UNITED STATES PATENT OFFICE
CERTIFICATE OF CORRECTION

Patent No. 4,123,335          Dated 10-31-78

Inventor(s) Seyl, Robert G.

It is certified that error appears in the above-identified patent and that said Letters Patent are hereby corrected as shown below:

Page 6 Line 11 from bottom permis should be changed to "permits"
Page 12 Line 12 from top o20 should be changed to "+20"
Page 12 Line 9 from bottom xb should be changed to "$i_{xb}$"
Page 14 Line 30 from top b, should be "ib"
Page 14 Last Line methos should be changed to "methods"
Page 15 Line 34 ]ir should be without ], "ir"
Page 15 Line 45 .=(1x10$^{31}$ 6)(50,000) should be "=(1x10-6)(50,000)
Page 15 Line 61 em=o.909-0.045=should be "em=0.090-0.045"
Page 16 Line 9 from top "0.45 + 0.020 = 0.115 volt" should be
-- 0.45 + 0.050 + 0.020 =0.115 volt.
Page 16 Line 40 k ir, should be "k ir' "

UNITED STATES PATENT AND TRADEMARK OFFICE
CERTIFICATE OF CORRECTION

PATENT NO. : 4,123,335

DATED : 10-31-78

INVENTOR(S) : Seyl, Robert G.

It is certified that error appears in the above-identified patent and that said Letters Patent are hereby corrected as shown below:

Claim 15 in the patent was claim 19 in the application which was dependent from claim 6, but during the renumbering of the claims after allowance, claim 6 in the application became claim 10 and therefore patent claim 15 should be made dependent from claim 10 of the patent.

Claim 22 in the patent was claim 14 in the application which was dependent from claim 11, but when the claims were renumbered after allowance, claim 11 became claim 18 and therefore patent claim 22 should be made dependent from claim 18 of the patent.

Also, in column 24 of the patent, line 16, "electrode" should read --electronic-- to accord with the record of the application.

The inventors given name is set out in the patent heading as "Rogert" and this should be corrected to read --Robert--.

In Table 4 appearing in columns 13 and 14 the line underlying "Voltage Separation" should extend from "$k_{ir}$", where the line starts, to overly "30-31" as indicated in this table appearing on page 27 of the application.

Column 15, line 46, the equation "$(1x10^{31}\ 6)$ should read --$(1x10^{-6})$--

UNITED STATES PATENT AND TRADEMARK OFFICE
CERTIFICATE OF CORRECTION

PATENT NO. : 4,123,335

DATED : 10-31-78

INVENTOR(S) : Seyl, Robert G.

It is certified that error appears in the above-identified patent and that said Letters Patent are hereby corrected as shown below:

Column 16, line 39, the figure "300.23% should be --+0.23%--

In line 49 of this column, the equation "$K_{ir}= rre/R_i$" should read --$K_{ir}=rre/R_i$--, Signed and Sealed this Seventeenth Day of July 1979

[SEAL]

Attest:

LUTRELLE F. PARKER

Attesting Officer — Acting Commissioner of Patents and Trademarks